United States Patent [19]

Curran et al.

[11] Patent Number: 5,230,345
[45] Date of Patent: Jul. 27, 1993

[54] METHOD FOR DETECTING CARPAL TUNNEL SYNDROME

[76] Inventors: Thomas M. Curran, 464 Springbrook Crescent; Terry J. Stefanski, 475 N. Maple, both of Saline, Mich. 48176; June S. Lai, 933 Robin Hood Road, Bloomfield Hills, Mich. 48304

[21] Appl. No.: 816,348

[22] Filed: Dec. 30, 1991

[51] Int. Cl.⁵ .............................................. A61B 5/00
[52] U.S. Cl. ...................................... 128/739; 128/744
[58] Field of Search ............... 128/739, 741, 742, 744; 73/662, 663; 364/413.02

[56] References Cited

U.S. PATENT DOCUMENTS

| | | | |
|---|---|---|---|
| 2,625,152 | 1/1953 | Frohring | 128/739 |
| 2,742,035 | 4/1956 | Hancock et al. | 128/739 |
| 4,175,546 | 11/1979 | Goldblatt et al. | 128/739 |
| 4,275,744 | 6/1981 | Thornton et al. | 128/731 |
| 4,641,661 | 2/1987 | Kalarickal | 128/744 |
| 5,002,065 | 3/1991 | Lacourse et al. | 128/739 |
| 5,022,407 | 6/1991 | Horch et al. | 128/739 |

FOREIGN PATENT DOCUMENTS 2846859 5/1979 Fed. Rep. of Germany ...... 128/739
1503745 8/1989 U.S.S.R. ........................... 128/739

OTHER PUBLICATIONS

Carlson et al. "Instrument for Measurement of Sensory Loss in the Fingertips" J. of Occupational Med. vol. 21 No. 4 Apr. 1979.

*Primary Examiner*—Max Hindenburg
*Assistant Examiner*—Guy V. Tucker
*Attorney, Agent, or Firm*—Brooks & Kushman

[57] ABSTRACT

A system and method is provided for detecting carpal tunnel syndrome in a patient, utilizing a vibratory waveform having a discrete frequency and a variable amplitude. The system includes control circuitry (22) for generating an electrical signal having the discrete frequency and a computer (14), including a memory, for controlling the circuitry (22) to vary the amplitude of the electrical signal and to generate associated amplitude data for storage in the memory. The system also includes a speaker (20) for converting the electrical signal into the vibratory waveform. A finger (34) of the patient rests directly on the cone (32) of the speaker (20), so that the vibratory waveform is applied directly to the finger (34).

5 Claims, 7 Drawing Sheets

METHOD FOR DETECTING CARPAL TUNNEL SYNDROME

TECHNICAL FIELD

The present invention is related to detecting carpal tunnel syndrome and, more particularly, to a system and method for detecting carpal tunnel syndrome utilizing vibrometry.

BACKGROUND ART

As is known, people suffering from certain pathological conditions, such as carpal tunnel syndrome (CTS), have an impaired sensitivity to vibration. The prior art provides devices for detecting such conditions by testing the patient's ability to sense vibration in a body extremity, such as a finger or a hand.

For example, U.S. Pat. No. 4,175,546, issued to Goldblatt et al., discloses a complex device for measuring sensitivity to externally applied vibration. The device includes a pallometer having a head or tool which is mounted on an end of a balance lever that is supported by a knife edge. The knife edge is mounted beneath a table having a upright opening through which an operative tip of the head projects. A counterweight mounted on the beam urges the head upwardly to lightly engage a stop with the operative tip exposed. When the tip is engaged by a patient, the head can swing downwardly so that the pressure of the tip on the patient is constant regardless of the pressure the patient may exert on the table at the edges of the opening.

U.S. Pat. No. 4,641,661, issued to Kalarickal, discloses an electronic algesimeter adapted to determine, by cutaneous sensation, the threshold of pain experienced by a patient at any skin site on the body. The instrument includes a pointed probe and is used by an examiner who continuously increases the pressure applied by the probe point on the skin until the patient feels the stimulus, at which critical point the pressure indication is then held. Since the instrument provides a real-time continuous readout, the muscular coordination of the examiner is not a factor.

U.S. Pat. No. 5,002,065, issued to LaCourse et al., discloses a vibratory screening or diagnostic system for diagnosing a patient to measure sensory disturbances of the patient. The system includes a vibratory stimulator for applying controlled and compensated vibratory forces to a finger, or other body portion, of the patient and a drive mechanism connected to effect vibration of the vibratory stimulator and operable to automatically effect discrete, but variable, vibrations at many frequencies over a wide range of frequencies and at variable amplitude levels at each frequency. The system also includes a response mechanism which permits the patient to record the onset of sensing by the patient of vibrations at each vibratory frequency.

The vibratory screening system of the LaCourse patent teaches a rather complex electrical and mechanical structure which requires a substantial amount of input information, such as the temperature of the fingertip skin, the pressure applied by the patient to the device and the wrist angle during testing, to function as described. Such a system is not only very costly, but is prone to diagnostic inaccuracies, since the results are based on many variables.

DISCLOSURE OF INVENTION

It is therefore an object of the present invention to provide a system and method for detecting carpal tunnel syndrome having a low cost and high diagnostic accuracy.

In carrying out the above objects and other objects of the present invention, a system is provided for detecting carpal tunnel syndrome in a patient. The system includes signal generating means for generating an electrical signal having a discrete frequency and control means, including a memory, for controlling the signal generating means to vary the amplitude of the electrical signal and to generate associated amplitude data for storage in the memory. The system also includes converting means for converting the electrical signal into a corresponding vibratory waveform. The converting means receives the finger of the patient such that the vibratory waveform is applied to the finger.

In further carrying out the above object and other objects and features of the present invention, a method is provided of detecting carpal tunnel syndrome in a patient. The method includes the steps of generating an electrical signal having a discrete frequency and providing an electroacoustic transducer for converting the electrical signal into a corresponding vibratory waveform, the transducer also for receiving a finger of the patient. The method also includes applying the electrical signal to the electroacoustic transducer to vibrate the finger and varying the amplitude of the electrical signal such that the patient senses the vibratory waveform.

The advantages accruing to the system and method of the present invention are numerous. For example, system componentry is minimized resulting in a low-cost and accurate diagnostic tool.

The above objects and other objects and features of the invention will be readily appreciated by one of ordinary skill in the art from the following detailed description of the best mode for carrying out the invention when taken in connection with the following drawings.

BEST MODE FOR CARRYING OUT THE INVENTION

Figure 1:
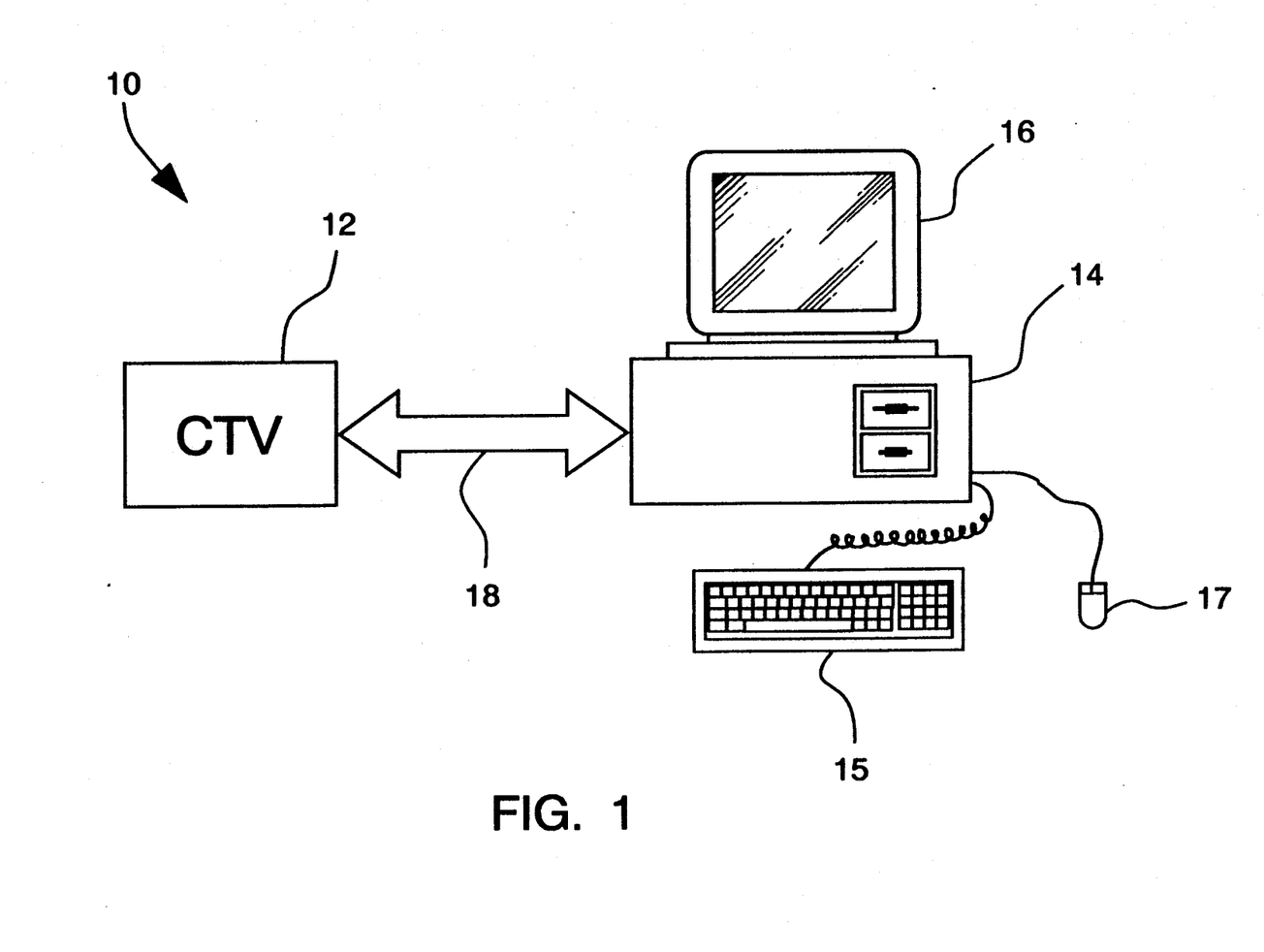
FIG. 1 is a block diagram of the system for diagnosing carpal tunnel syndrome according to the present invention.

Referring now to FIG. 1, there is illustrated a system, shown generally by reference number 10, for detecting carpal tunnel syndrome in a finger or other body part of a patient. In the preferred embodiment, the system 10 includes a carpal tunnel vibrometer (CTV) 12 and a computer 14. The computer 14, such as a commercially available IBM personal computer or the like, preferably includes a monitor 16 and communicates with the carpal tunnel vibrometer 12 through the wiring 18. The computer 14 also preferably includes an digital-to-analog (D/A) board (not specifically illustrated) such as the DAC-02, available from the Keithley Metrabyte Corporation, Taunton, Mass.

Figure 2:
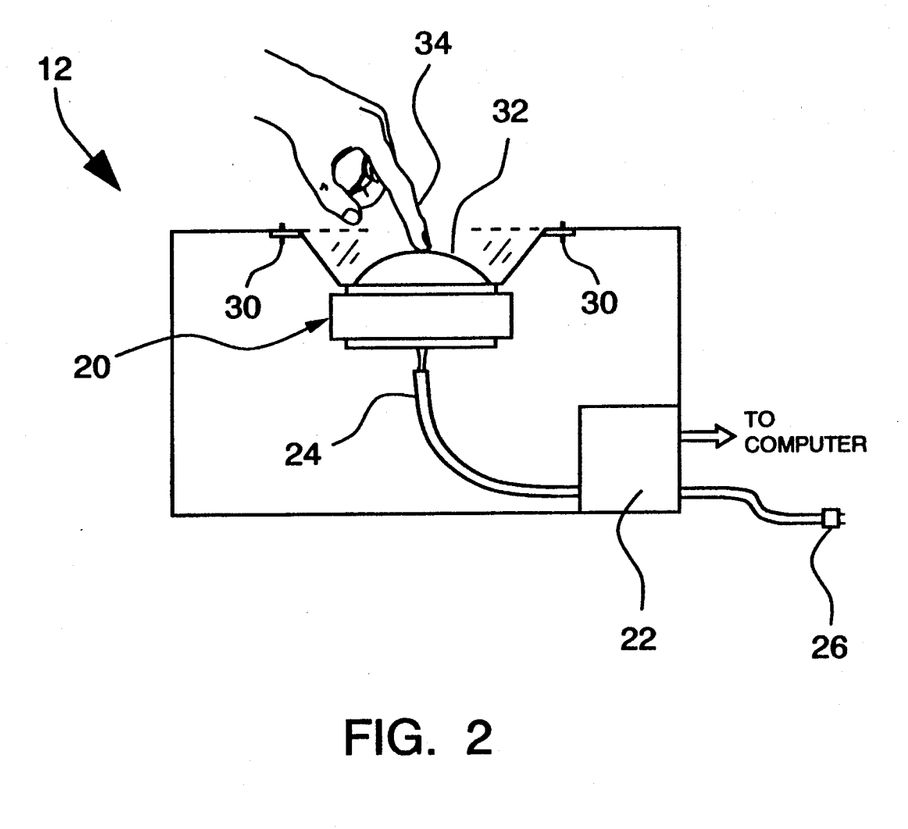
FIG. 2 is a cross-sectional view of the carpal tunnel vibrometer (CTV) shown in FIG. 1, taken along line 2—2.

As best shown in FIG. 2, the CTV 12 preferably includes an electroacoustic transducer, or speaker, 20 electrically connected to the control circuitry 22 through wiring 24. The CTV 12 is powered through a standard, commercially available 115 VAC-to-12 VAC wall transformer 26.

In the preferred embodiment, the speaker 20 is fixedly attached to the CTV 12 by screws 30, or the like, and has a single plastic cone 32, which directly receives a finger 34 being tested. As is known, speaker 20 converts an electrical signal from the control circuitry 22 into a vibratory waveform, which waveform is then applied to the finger 34, as described in greater detail hereinbelow.

Figure 3:
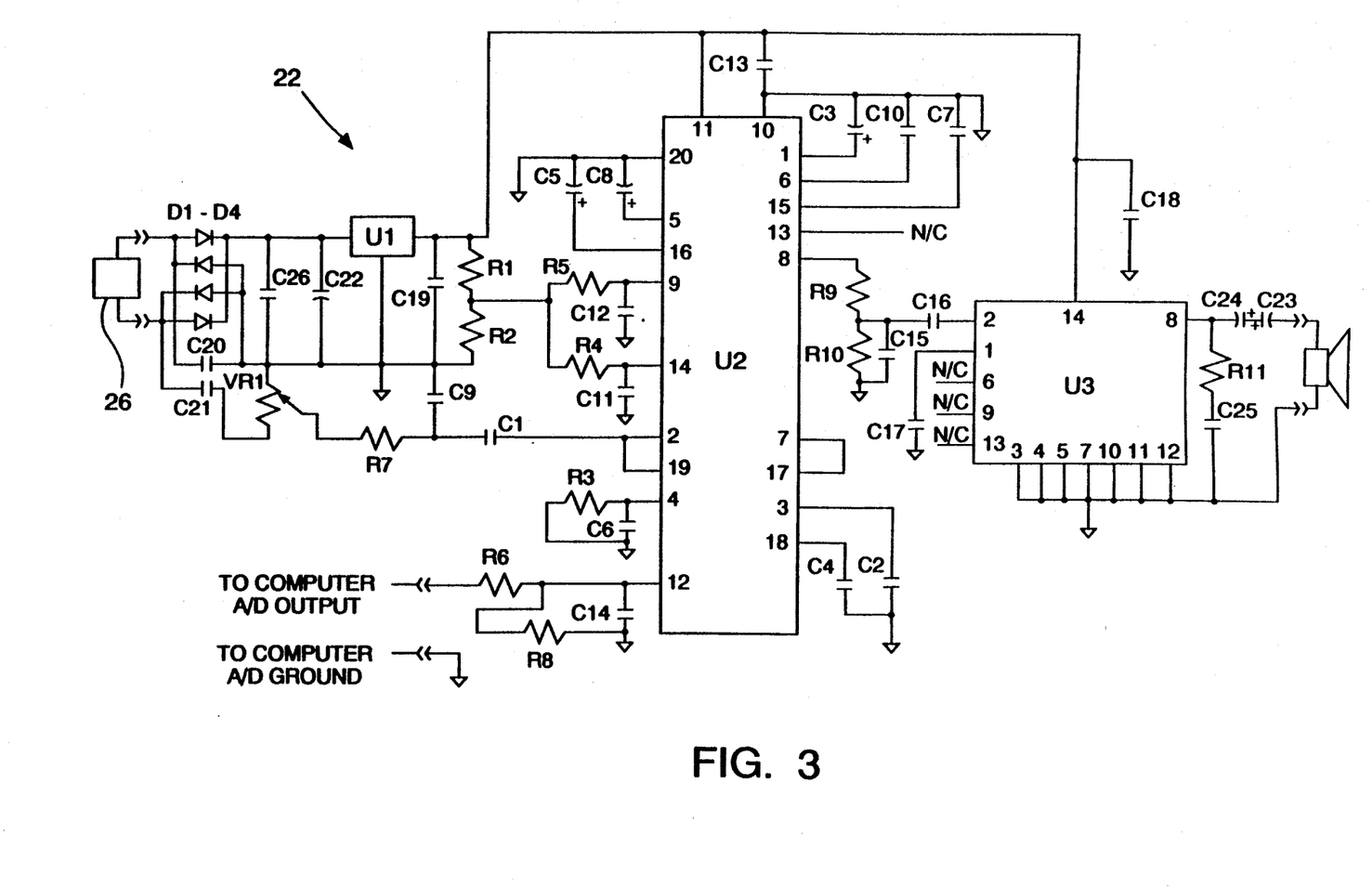
FIG. 3 is a schematic representation of the signal generating circuitry for use with the present invention.

Referring now to FIG. 3, there is shown a schematic representation of the control circuitry 22. The transformer 26 provides a 12 V, 60 Hz signal to the circuitry 22. Diodes D1 through D4, such as P/N 1N4001, function as a bridge rectifier to the 12 V, 60 Hz signal. The rectified signal is then regulated by a 12 V regulator U1, such as the LM7812, commercially available from National Semiconductor. Capacitors C26 and C22 act as a filter, while capacitors C20 and C21 function as a pickup for the DC-isolated 60 Hz AC waveform that is applied to the potentiometer VR1. Capacitor C9 and resistor R7 function as a bypass filter and capacitor C1 further DC isolates the signal, which is then applied to a voltage controlled attenuator U2.

The voltage controlled attenuator U2, such as an LM1036, commercially available from National Semiconductor, provides a dual tone-balance volume control. In the preferred embodiment, however, only one channel is utilized to drive the speaker 20. The voltage controlled attenuator U2 is controlled by a 0 V-10 V analog signal from the D/A board of the computer 14 applied to the attenuator U2 at input pin 12. Resistors R6 and R8 function as a voltage divider to divide the 0 V-10 V signal from the computer 14 to a 0 V-5 V signal compatible with the voltage controlled attenuator U2. Preferably, a 0 V signal from the computer 14 corresponds to a minimum speaker amplitude and a 10 V signal from the computer 14 corresponds to the maximum amplitude.

In the preferred embodiment, resistors R5 and R4 operate to set the balance of the attenuator U2 at approximately zero decibels (dB). Resistor R3 operates to set the treble to a value of −12 dB, since the speaker 20 is operated at a low frequency.

The output of the voltage controlled attenuator U2 (i.e. pin 8) is coupled to a small audio amplifier U3, such as an LM380, commercially available from National Semiconductor. Since the amplifier U3 has a fixed gain, the output of the attenuator U2 is preferably reduced by the R9 and R10 voltage divider. The control circuitry 22 functions best with DC blocking capacitors C23 and C24 connected to the output pin of the amplifier U3, since the amplifier U3 has an offset output. Resistor R11 and capacitor C17, C18 and C25 function to stabilize the operation of the amplifier U3. The output signal of the amplifier U3 thus has a fixed frequency of 60 Hz and a variable amplitude.

Figure 4A:
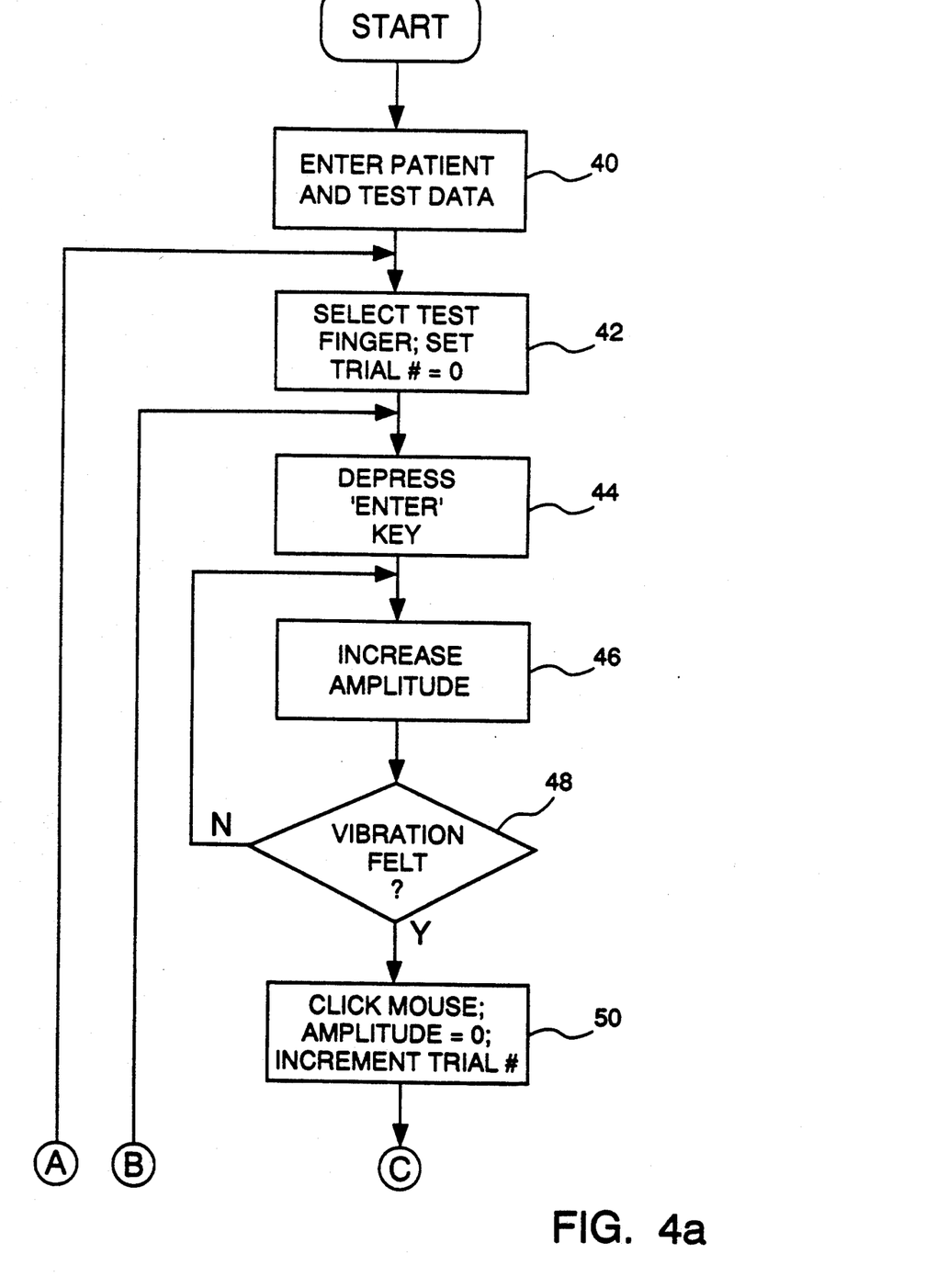
FIGS. 4a–4b are a flow chart illustrating the steps for diagnosing carpal tunnel syndrome in a patient according to the present invention.
Figure 4B:
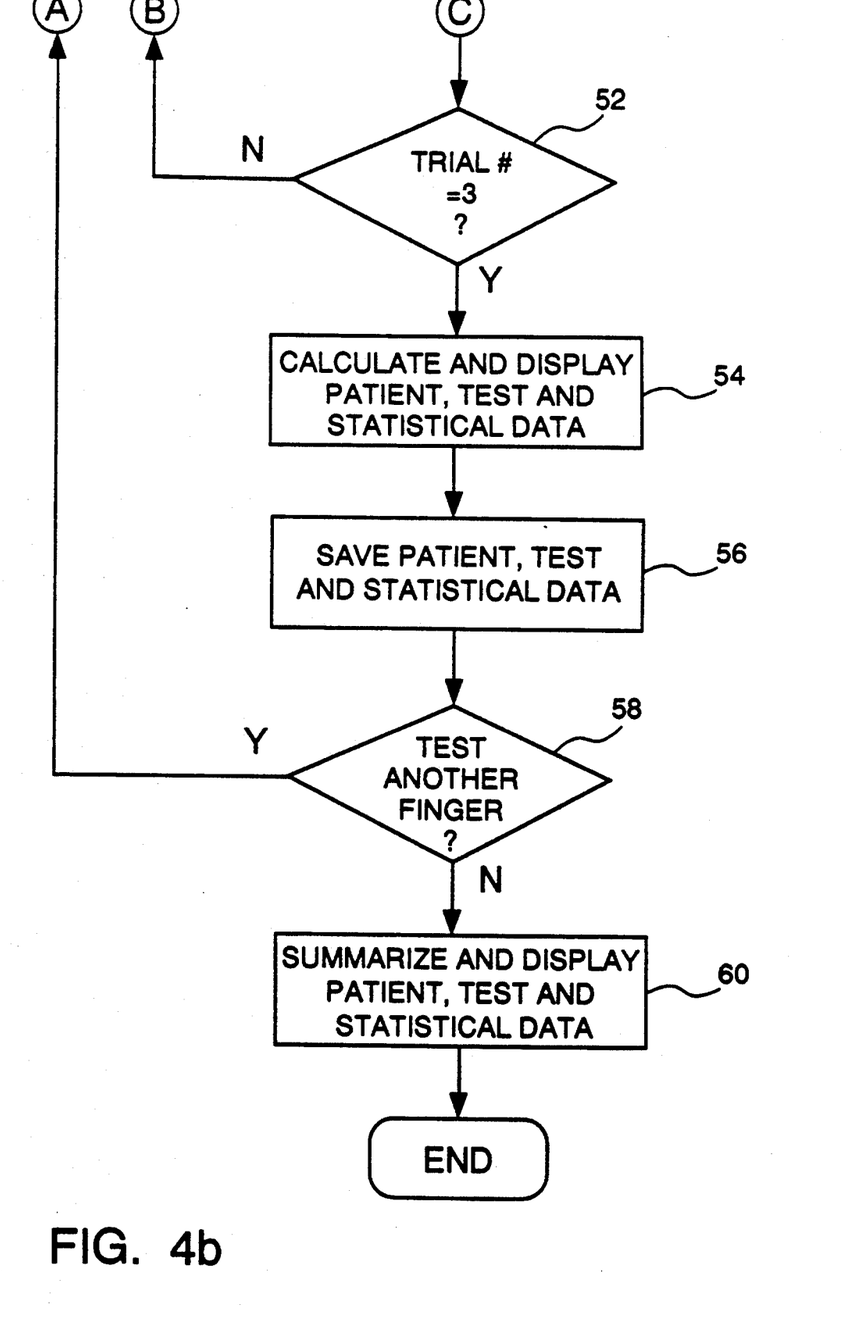

Referring now to FIGS. 4a–4b, there is shown a flow chart illustrating the steps for diagnosing carpal tunnel syndrome in a patient, according to the present invention. At step 40, the operator enters the patient and test data into the computer 14. Preferably, the patient data is biographical in nature and includes patient name and identification number, age and gender. The test data preferably includes test technician name, which finger is being tested and the date and time of the test.

At step 42, the operator selects the finger to be tested from a scrollable menu, not specifically illustrated, on the monitor 16. The patient places the tip of the finger to be tested directly on the cone 32 of the speaker 20, as best shown in FIG. 2. The carpal tunnel vibrometer 12 functions best if the patient simply rests the finger on the cone 32. The software then sets a trial number variable, utilized to keep track of the number of tests performed on the finger, equal to zero ("0").

Once the test finger has been selected, the software displays an X-Y graph on the monitor 16, which provides a real-time graphical representation of the amplitude of the vibratory waveform applied to the test finger. In the preferred embodiment, the trial number is represented along the X axis and the signal amplitude is represented along the Y axis.

The carpal tunnel test is initiated at step 44 when the operator depresses the 'ENTER' key on the computer keyboard 15. An electrical signal having a discrete, or fixed, frequency of about 60 hertz (Hz) and a nominal (i.e. zero) amplitude is generated by the control circuitry 22, as described above, and applied to the speaker 20. The speaker 20 converts the electrical signal to an associated vibratory waveform.

At step 46, the amplitude of the vibratory waveform is preferably increased by a value of one decibel (dB) per second by the computer, which controls the LM1036 voltage controlled attenuator, as described in greater detail above. As the amplitude is increased, the graph on the monitor increases. The amplitude of the waveform is increased until, at step 48, the patient feels the vibration.

At step 50, the patient responds to the sensed vibration by "clicking" the mouse 17, which provides a control signal to the computer. Of course, the patient could respond to the vibration sensed in some other fashion, such as depressing a key of the keyboard or the like. Once the vibration is sensed, the computer 14 resets the amplitude of the waveform to "zero", increments the trial number variable by one (1), and the first trial for the finger tested is complete.

In the preferred embodiment, steps 44 through 50 are performed three times for each finger tested. At step 52, the value of the trial number variable is checked to determine how many tests have been performed on each finger. If the finger has been tested three times, the computer utilizes the results to calculate and display statistical data at step 54.

Figure 5:
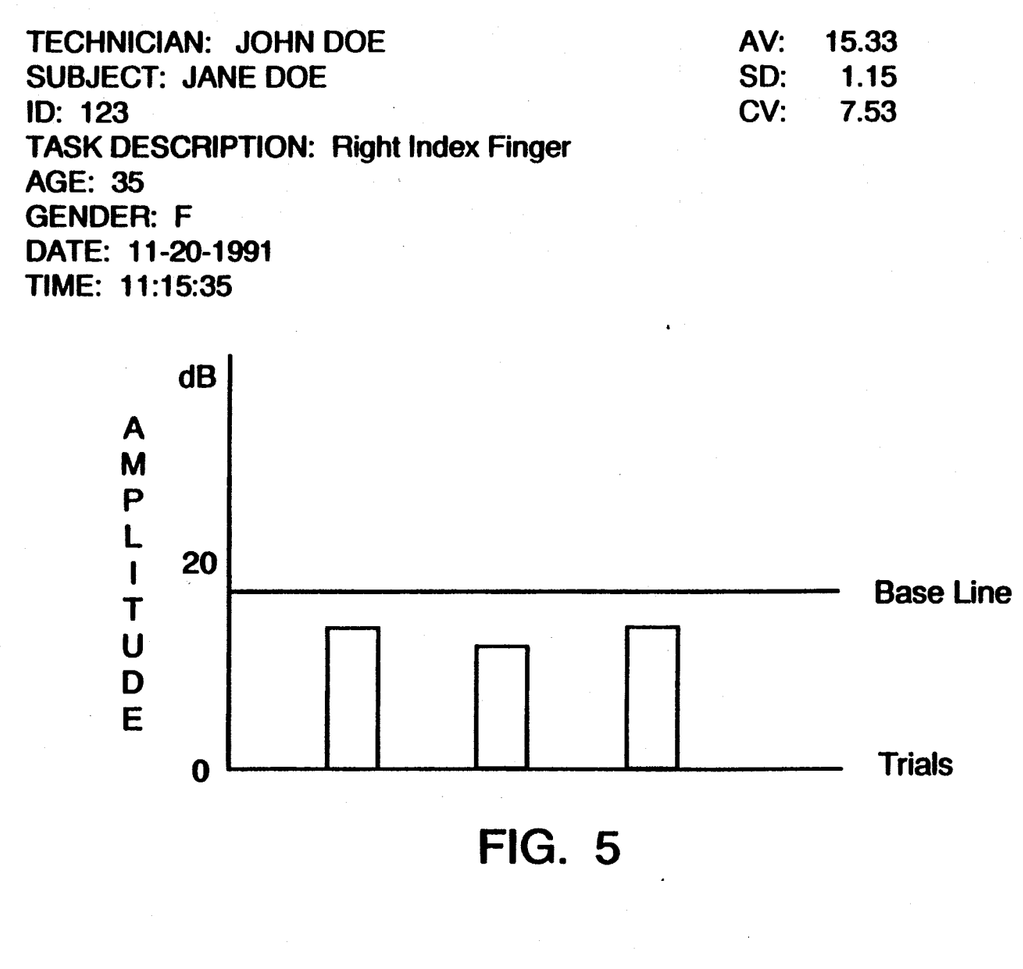
FIG. 5 is an illustration of the bar graph and other data displayed after testing a single finger, utilizing the CTV of the present invention.

As best shown in FIG. 5, the three measured peak amplitudes are preferably displayed as an easy-to-read bar graph in relation to the "base line" amplitude. Generally, measured amplitudes exceeding the base line indicate a diseased condition in the patient.

As illustrated, the display also includes the patient and test data entered at step 40 and statistical data based on the test results. The statistical data, which includes the average (AVG), standard deviation (SD) and coefficient of variation (CV) of the three measured peak amplitudes, is calculated as follows:

$$AVG = \frac{\Sigma(Peaks)}{No.\ of\ Trials}$$

$$SD = \frac{(\Sigma Peaks)^2 - ((\Sigma Peaks)^2/No.\ of\ Trials)}{No.\ of\ Trials - 1}$$

$$CV = \left(\frac{SD}{AVG}\right) * 100$$

At step 56, the computer saves the patient, test and statistical data in a memory, such as a random access memory (RAM). At step 58, the operator indicates whether or not another finger is to be tested by preferably depressing the 'ESCAPE' key which results in the scroll menu being displayed on the monitor 16. Steps 42-56 would thus be repeated, as previously described, for additional fingers being tested. As additional fingers tested, the operator can recall and view the test results for each finger tested utilizing the arrow keys of keyboard 15.

At step 60, the test data for the various fingers tested is summarized. Preferably, this summarization includes retrieving the stored patient, test and statistical data from the RAM memory for display. Also, grand total statistical calculations are performed utilizing the data from each finger tested.

Figure 6:
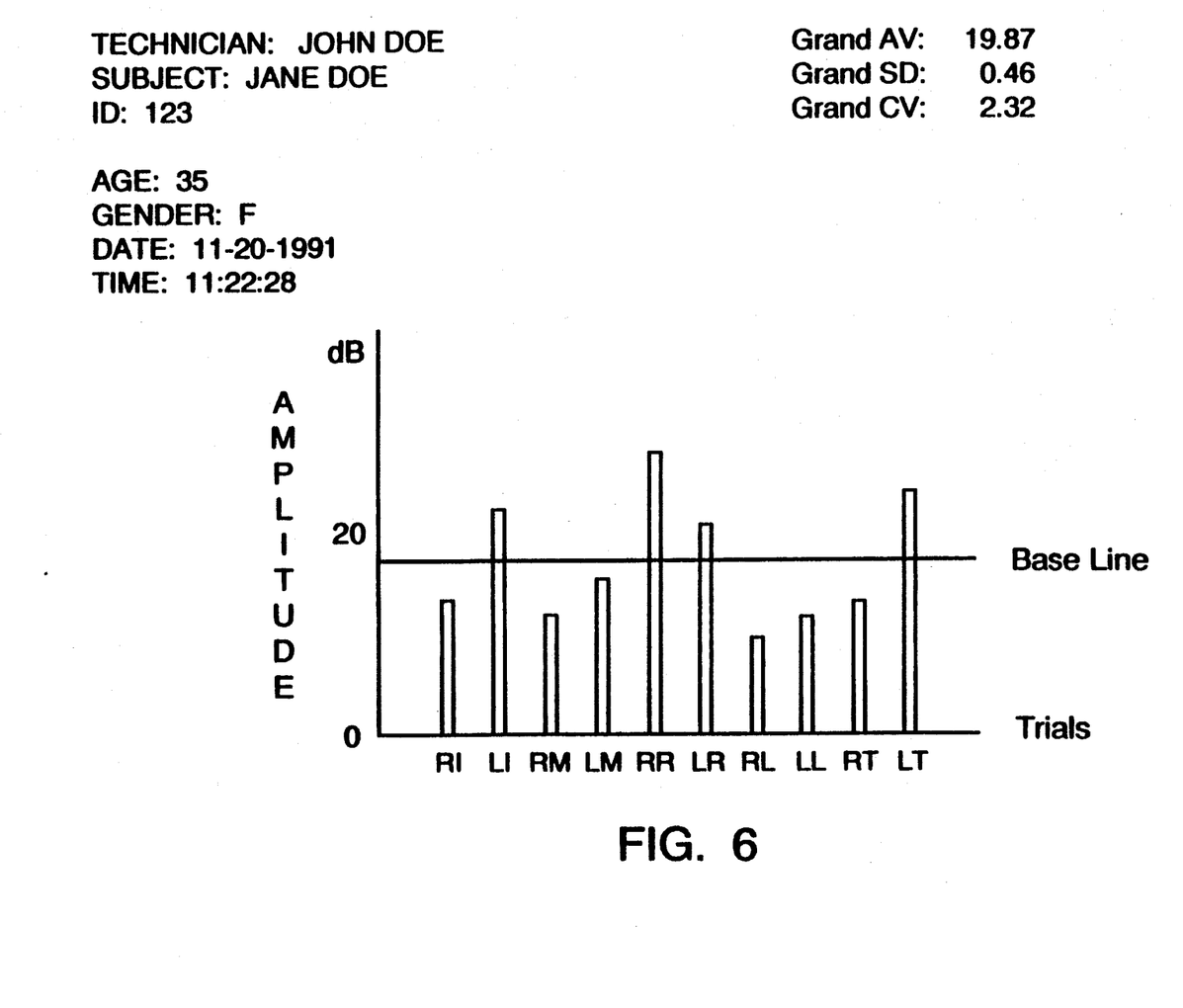
FIG. 6 is an illustration of the summary bar graph and other data displayed at the completion of testing, utilizing the CTV of the present invention.

As best shown in FIG. 6, the statistical data summarization for the fingers tested is displayed on the monitor 16. In the preferred embodiment, the average amplitudes for each finger tested are displayed as a bar graph on a single screen, allowing the operator to quickly and accurately perform a right-left comparison of the fingers tested. The grand total statistical calculations of the average, standard deviation and coefficient of variation are also displayed.

It is understood, of course, that while the form of the invention herein shown and described constitutes the preferred embodiment of the invention, it is not intended to illustrate all possible forms thereof. It will also be understood that the words used are words of description, rather than limitation, and that various changes may be made without departing from the spirit and scope of the invention as disclosed.

What is claimed is:

1. A method for assisting in the diagnosis carpal tunnel syndrome in a patient, the method comprising:
   providing a plastic cone speaker for converting an electrical signal into a corresponding vibratory waveform;
   positioning a finger of the patient to be tested directly on the speaker cone;
   generating the electrical signal, the signal having a fixed frequency;
   energizing the speaker according to the electrical signal, the speaker generating the vibratory waveform to vibrate the finger;
   increasing the amplitude of the electrical signal from an initial amplitude until the patient detects vibration from the speaker at a final amplitude; and
   generating a control signal by the user to indicate detection of vibration, the amplitude of the electrical signal being reset to the initial amplitude based on the control signal.

2. The method of claim 1 further comprising generating amplitude data based on the amplitude of the electrical signal and storing the amplitude data in a data storage device.

3. The method of claim 2 further comprising processing the amplitude data to obtain statistical data and storing the statistical data in the data storage device.

4. The method of claim 3 further comprising displaying the amplitude data and the statistical data on a display.

5. The method of claim 1 wherein the step of generating includes generating a signal having a frequency of 60 Hz.

* * * * *